United States Patent [19]
Gunther

[11] 4,098,573
[45] * Jul. 4, 1978

[54] PORTABLE MOISTURIZATION AND STERILIZATION

[75] Inventor: Donald A. Gunther, Erie, Pa.

[73] Assignee: American Sterilizer Company, Erie, Pa.

[*] Notice: The portion of the term of this patent subsequent to Feb. 3, 1993, has been disclaimed.

[21] Appl. No.: 705,805

[22] Filed: Jul. 16, 1976

[51] Int. Cl.² .......................... A61L 5/00; A61L 3/00
[52] U.S. Cl. .................................... 21/93; 21/57; 21/94; 21/103; 21/91; 21/DIG. 4; 261/69 R; 261/142
[58] Field of Search ............... 21/DIG. 4, 57, 91, 92, 21/93, 103, 94–98; 261/69 R, 142

[56] References Cited
U.S. PATENT DOCUMENTS

| | | | |
|---|---|---|---|
| 3,068,064 | 12/1962 | McDonald | 21/DIG. 4 UX |
| 3,088,179 | 5/1963 | Leuthner | 21/DIG. 4 UX |
| 3,687,612 | 8/1972 | Ernst | 21/DIG. 4 X |
| 3,753,651 | 8/1973 | Boucher | 21/DIG. 4 X |
| 3,826,612 | 7/1974 | Black | 21/103 X |
| 3,910,761 | 10/1975 | Hopkins | 21/DIG. 4 X |
| 3,916,891 | 11/1975 | Freytag et al. | 261/142 X |
| 3,936,270 | 2/1976 | Gunther | 21/DIG. 4 X |
| 3,954,406 | 5/1976 | Chamberlain | 21/DIG. 4 X |

*Primary Examiner*—Barry S. Richman
*Attorney, Agent, or Firm*—Charles L. Lovercheck

[57] ABSTRACT

A method and apparatus for humidifying a product in a microbiocidal gas sterilizing process wherein a predetermined amount of water is admitted to the chamber through a capillary tube controlled by a pressure controlled valve, and control system therefor, which is actuated by a decrease in the total pressure within the sterilization chamber below a predetermined value. Once the pressure again rises to said predetermined value, the valve will be closed, thereby permitting a controlled humidity level to be maintained in the chamber.

1 Claim, 2 Drawing Figures

PORTABLE MOISTURIZATION AND STERILIZATION

GENERAL DESCRIPTION OF THE INVENTION

Humidification in small, portable EtO sterilizers is usually accomplished by pouring water on the floor of the sterilizer and using the heat of the shell to vaporize the water; the water is added in a fixed quantity, so there is no means of controlling or insuring proper humidity with different loads. Also, the comparatively low temperature of the shell does not vaporize the water readily and thus humidification is slow.

This disclosure describes a rapid method of humidification which is controlled by a pressure sensitive switch that monitors the total pressure within the sterilizer.

Water is converted to steam by means of a metal sheath, extending into the sterilizer via a standard threaded bushing, which is heated by an electric probe heater inserted in the sheath. A small boat is attached to the sheath in a manner to provide good thermal contact (such as brazing); water is added to this boat in a controlled manner, and is converted to steam by the heated sheath. The addition of water to the boat on the sheath is achieved by means of a reservoir attached to the outside of the sterilizer with a communicating capillary tube extending into the sterilizer and positioned over the water-containing boat on the sheath. The rate of water addition via the capillary tube, and the rate of vaporization, are adjusted so that the vaporized water (steam) has an opportunity to penetrate the load before reaching a sufficiently high vapor pressure in the chamber to trigger the pressure sensitive monitoring switch (alternatively, a time-delay relay could be used to delay activation of the pressure sensitive switch).

REFERENCE TO PRIOR ART

U.S. Pat. No. 3,068,064 shows a method and apparatus for sterilizing wherein a known quantity of water, sufficient to humidify the atmosphere in a sterilizer, is evaporated by a heater and drawn into the chamber by the vacuum produced in the chamber, the effect being that the entire quantity of water is drawn into the chamber at one time as a single quantity of steam with no regulation of the relative humidity or the vapor pressure of water at any one time. The present invention provides a method and apparatus for introducing the water to a sterilizer at a rate that will maintain the total pressure in the chamber at a predetermined value.

OBJECTS OF THE INVENTION

It is an object of the invention to provide an improved method and apparatus for moisturizing a product prior to sterilization.

Another object of the invention is to provide a method and apparatus for moisturizing a product prior to sterilization that is simple in construction, economical to manufacture and simple and efficient to use.

With the above and other objects in view, the present invention consists of the combination and arrangement of parts hereinafter more fully described, illustrated in the accompanying drawing and more particularly pointed out in the appended claims, it being understood that changes may be made in the form, size, proportions and minor details of construction without departing from the spirit or sacrificing any of the advantages of the invention.

GENERAL DESCRIPTION OF THE DRAWINGS

DETAILED DESCRIPTION OF THE DRAWINGS

Figure 1:
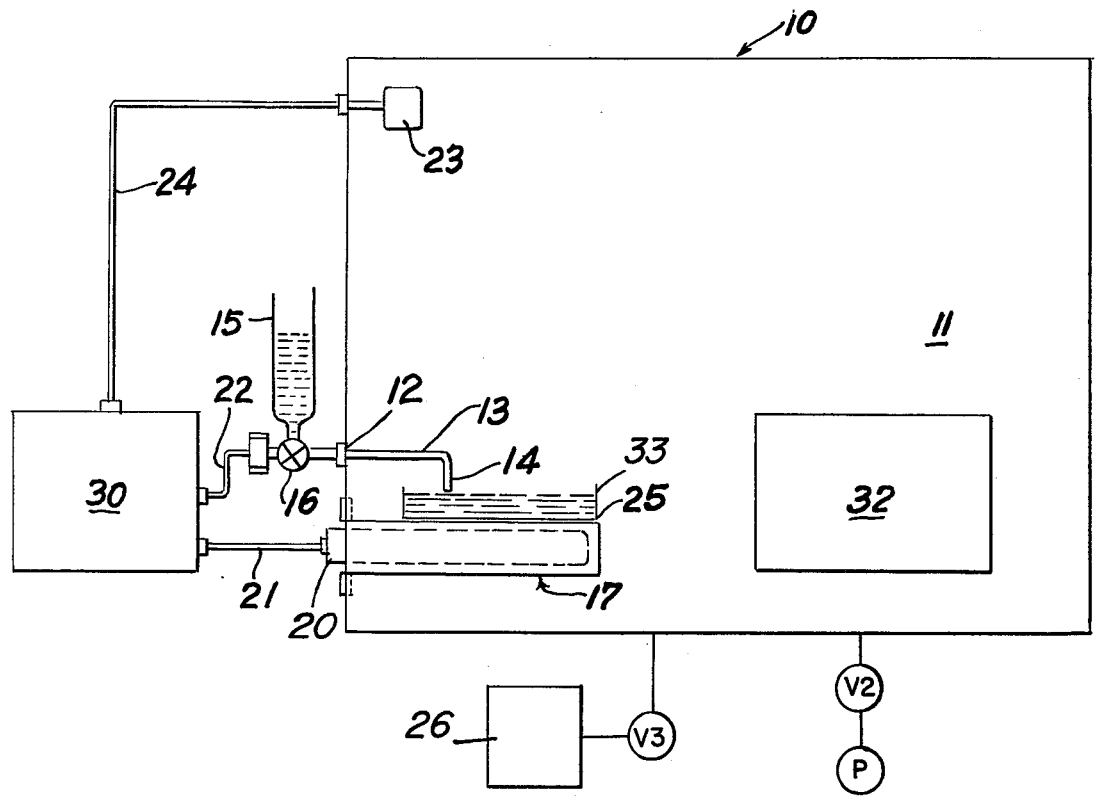
FIG. 1 is a diagramatic view of the apparatus for humidifying according to the invention.
Figure 2:
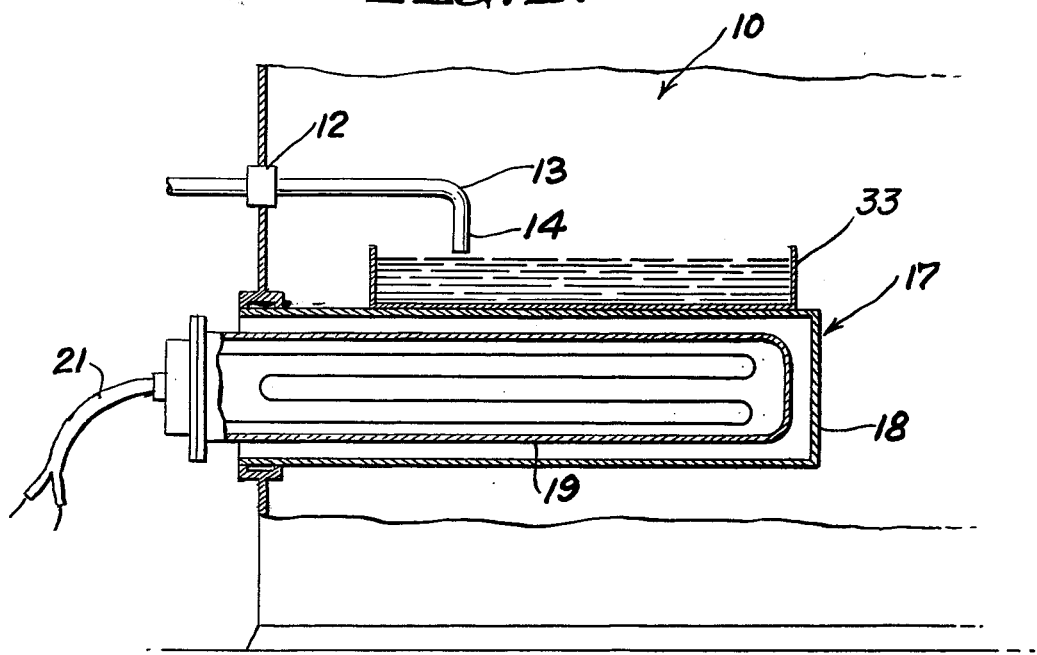
FIG. 2 is an enlarged view of a part of the apparatus shown in FIG. 1.

Now, with more particular reference to the drawings, an apparatus is shown including a chamber 10 which may be any of the well known types of autoclaves used for sterilizing familiar to those skilled in the art. The chamber 10 is provided with a suitable sealable door 11 for loading the chamber with products to be sterilized. An opening 12 in the chamber wall, with a suitable bushing, admits the capillary tube 13 which has a downwardly-disposed discharge end 14 adapted to discharge water from the bottle 15 through valve 16 and through capillary tube 13, then out discharge end 14 of capillary tube 13 and into the boat 33. Boat 33 is supported on a sheath 18 which is in thermal-conducting relation to the heater 19. The sheath 18 is passed through the bushing 20 which provides seal between the chamber 10 and the heater 19. Heater 19 may be any of a number of suitable electrical heating units familiar to those skilled in the art.

The heater 19 is connected to a suitable control 30 through a line 21. Control 30 will likewise be provided to connect the solenoid valve 16 through line 22 to control 30 and the solenoid valve 16 is actuated by a pressure-sensitive switch 23 connected, via line 24, to control 30.

The boat 33 which is an open-topped container is connected to the metal sheath 18 by a material that will be a good conductor of heat, e.g. brazing or the like, indicated at 25. A gas dispenser 26 is connected to the chamber through a shut-off valve V-3 and a pump P is connected to the chamber through a shut-off valve V-2 whereby the chamber can be evacuated.

To carry out the process, the product to be sterilized, indicated at 32, is introduced into the chamber and the door 11 is closed and sealed. The operator then puts a measured quantity of water into the bottle 15, sufficient to moisturize the load 32 to the desired extent. The operator then actuates the control 30 and at this point, the pressure in the chamber is atmospheric. Control 30 will actuate both the heater 19 and the solenoid valve 16 so that water from bottle 15 will enter the chamber 10 through capillary tube 13 into boat 33 where it will be evaporated by heat from heater 19. The vapor pressure of the evaporating water will increase inside the chamber until it reaches a point where it actuates the pressure-sensitive switch 23 which will deactivate valve 16, causing it to close. As the load 32 absorbs moisture, the vapor pressure in the chamber will decrease thereby decreasing the total pressure and the pressure switch 23 will again actuate valve 16 and heater 19, introducing more water through capillary tube 13.

This process continues until sufficient water has been introduced to the chamber 10. After moisturization, a microbiocidal chemical sterilizing gas is introduced into the chamber 10 in a manner familiar to those skilled in the art. The chamber may be evacuated by pump P and valve V2 during or after moisturization, and sterilizing gas may be admitted through valve V3 from gas dispenser 26.

The foregoing specification sets forth the invention in its preferred practical forms but the structure shown is capable of modification within a range of equivalents without departing from the invention which is to be understood is broadly novel as is commensurate with the appended claims.

The embodiments of the invention in which an exclusive property or privilege is claimed are defined as follows:

1. An apparatus for moisturizing and sterilizing articles comprising:

a chamber adapted to be loaded and sealed, a first container for water in said chamber, a second container outside said chamber, means to evacuate said chamber, means for introducing a microbiocidal chemical sterilizing gas into said chamber, capillary tube means connecting said first container to said second container, heating means operatively thermally connected to said first container for evaporating water contained therein, valve means operatively connected to said capillary tube means for controlling the flow of water from said second container to said first container, pressure control means in said chamber connected to said valve means for actuating said valve means for allowing water to flow through said capillary tube means into said chamber when the pressure in said chamber falls below a predetermined level due to absorption of water vapor by the articles located within the chamber, said control means deactivating said valve means when the pressure in the chamber rises in excess of said predetermined level.

* * * * *